United States Patent [19]

Darragh

[11] 4,072,684

[45] Feb. 7, 1978

[54] MANUFACTURE OF PYRIDINE AND METHYLPYRIDINES

[75] Inventor: John Irvine Darragh, Runcorn, England

[73] Assignee: Imperial Chemical Industries Limited, Great Britain

[21] Appl. No.: 760,143

[22] Filed: Jan. 17, 1977

[30] Foreign Application Priority Data

Feb. 2, 1976 United Kingdom .................. 3998/76

[51] Int. Cl.$^2$ ........................................... C07D 213/06
[52] U.S. Cl. .................................................. 260/290 P
[58] Field of Search ...................................... 260/290 P

[56] References Cited

U.S. PATENT DOCUMENTS

| 2,567,254 | 8/1946 | Teter | 260/290 P |
|---|---|---|---|
| 3,472,860 | 10/1969 | Hargrave | 260/290 P |

*Primary Examiner*—Alan L. Rotman
*Attorney, Agent, or Firm*—Cushman, Darby & Cushman

[57] ABSTRACT

The proportion of residual solvent in a solid chlorinated polymer prepared by chlorination in a chlorine-resistant solvent and subsequent treatment with steam or hot water is reduced by carrying out the said treatment in the presence of a polymer lubricant.

7 Claims, No Drawings

MANUFACTURE OF PYRIDINE AND METHYLPYRIDINES

This invention relates to the manufacture of pyridine and methylpyridines.

According to the present invention there is provided a process for the manufacture of pyridine and/or methylpyridines which comprises the catalytic vapour-phase reaction of 1,3-butadiene and methylamine.

Suitable catalysts for use in the process of the present invention include those known as catalysts for the vapour-phase reaction between formaldehyde acetaldehyde and ammonia, for example the dehydration and/or cracking catalysts described in the specification of UK Pat. No. 1,070,664.

It is preferred to use a catalyst comprising silicaalumina.

The catalyst may be employed either as a fixed bed or in the form of a fluidised bed.

The reaction may be carried out over a wide range of temperature, for example from 300° C to 500° C but the preferred temperatures are those in the range 300° C to 400° C.

The reaction is preferably carried out at substantially atmospheric pressure but higher or lower pressures may be used.

The molar ratio of methylamine to butadiene is preferably at least 0.5 to 1. It is especially preferred to use at least 1 mole of methylamine, for example from 1 to 5 moles of methylamine, per mole of butadiene.

The reaction is preferably carried out in the presence of nitrogen and/or another gaseous diluent (for example steam).

The proportion of pyridine (relative to ethylpyridines) in the product is in general increased by the incorporation of molecular oxygen in the reaction mixture. It is preferred to carry out the reaction in the presence of steam, for example at least 3 moles of steam for each mole of total organic reactants (butadiene and methylamine). While the proportion of steam may be considerably in excess of this ratio an upper limit will, in practice, be imposed by the desirability of maintaining an acceptably high throughput of the reactants. Thus while the proportion of steam may be for example, from 3 to 20 moles of steam per mole of total organic reactants there is in general little to be gained by using more than about 10 moles of steam per mole of total organic reactants.

Whether oxygen is added, and if so in what proportion, will depend upon whether it is desired to optimise the direct conversion into pyridine or whether it is preferred to optimise the conversion into total pyridine bases (including methylpyridines).

Even when pyridine itself is the product mainly desired it may sometimes be advantageous to optimise the conversion into total pyridine bases and subsequently subject the methylpyridines to demethylation.

The reaction products may conveniently be passed directly to a dealkylation process without an intermediate separation stage. Thus the reaction products (including pyridine and methylpyridines) may be maintained in the vapour phase and passed continuously to a stage wherein methylpyridines are demethylated in the presence of a dealkylation catalyst, which may be the same as, or different from, the catalyst employed in the stage of the primary reaction between methylamine and butadiene.

If desired, steam or further steam may be introduced at the demethylation stage (or between the primary stage and the demethylation stage). Molecular oxygen may also be introduced at the demethylation stage (or between the primary stage and the demethylation stage.)

Pyridine and/or methylpyridines may be separated from the reaction products by known methods, for example by distillation, extraction or a combination of such methods.

The invention is illustrated by the following Example.

EXAMPLE

A gaseous mixture consisting of 1,3 butadiene (1.0 part by volume), methylamine (2.2 parts by volume), air (16.8 parts by volumes), steam (21.9 parts by volume) and nitrogen (12.6 parts by volume) was passed through a fluidised bed of silica - alumina catalyst, commercially available as "Synclyst" (Trade Mark) — grade 3A MS/13/HD, maintained at 350° C. The contact time was 5 seconds.

The gases from the reaction zone were cooled to give a liquid product containing pyridine bases. The uncondensed gases were scrubbed with water to recover a further quantity of pyridine bases. The yield of pyridine (based on gram atoms of carbon fed) was 8.0% and the yield of 3-methylpyridine (on the same basis) was 0.4%.

What is claimed is:

1. A process for the manufacture of pyridine which comprises the vapour-phase reaction, in the presence of a catalyst comprising alumina-silica and at a temperature in the range from 300° C to 500° C, of 1,3-butadiene and methylamine in the presence of a gaseous diluent wherein there is employed at least 0.5 mole of methylamine per mole of butadiene.

2. A process as set forth in claim 1 in which methylpyridine also is produced.

3. A process according to claim 1 wherein the reaction is carried out at a temperature in the range from 300° C to 400° C.

4. A process according to claim 1 wherein at least 1 mole of methylamine is employed per mole of butadiene.

5. A process according to claim 1 wherein the gaseous diluent is steam.

6. A process according to claim 5 wherein the proportion of steam is at least 3 moles of steam per total mole of butadiene and methylamine.

7. A process according to claim 1 wherein the reaction mixture comprises molecular oxygen.

* * * * *